United States Patent
Petisce et al.

(10) Patent No.: US 10,799,621 B2
(45) Date of Patent: Oct. 13, 2020

(54) DEVICE AND METHOD FOR INHIBITING MOVEMENT OF A MEDICAL DEVICE IN A PATIENT

(71) Applicant: Becton, Dickinson and Company, Franklin Lakes, NJ (US)

(72) Inventors: James Petisce, Westford, MA (US); Nathaniel McCaffrey, Mill Valley, CA (US); Amit Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 481 days.

(21) Appl. No.: 14/654,493

(22) PCT Filed: Dec. 20, 2012

(86) PCT No.: PCT/US2012/070870
§ 371 (c)(1),
(2) Date: Jun. 19, 2015

(87) PCT Pub. No.: WO2014/098864
PCT Pub. Date: Jun. 26, 2014

(65) Prior Publication Data
US 2015/0328370 A1    Nov. 19, 2015

(51) Int. Cl.
*A61L 29/08* (2006.01)
*A61M 25/00* (2006.01)
(Continued)

(52) U.S. Cl.
CPC ........ *A61L 29/085* (2013.01); *A61B 5/14503* (2013.01); *A61B 5/14532* (2013.01);
(Continued)

(58) Field of Classification Search
None
See application file for complete search history.

(56) References Cited

U.S. PATENT DOCUMENTS 3,648,704 A * 3/1972 Jackson .............. A61M 25/002
604/172
4,664,657 A    5/1987 Williamitis et al.
(Continued)

FOREIGN PATENT DOCUMENTS

JP    2005-515838    6/2005
WO    WO 9903424 A1 *  1/1999 ............. A61L 15/58

OTHER PUBLICATIONS

European Office Action dated Jun. 22, 2017 which issued in the corresponding Patent Application No. 12 890 542.9.
(Continued)

*Primary Examiner* — Matthew Kremer
(74) *Attorney, Agent, or Firm* — Dickinson Wright PLLC

(57) ABSTRACT

A medical device such as a cannula, catheter, needle or biosensing probe includes an elongated body for penetrating, inserting and/or positioning in or through the skin of a patient. The elongated body has an outer surface that when positioned in the patient with a coefficient of friction sufficient to inhibit movement between the elongated body on the skin at the insertion site to inhibit irritation at the infusion site. A lubricious coating is provided on the elongated body to assist in penetration and/or insertion of the elongated body into the patient. The lubricious coating can be removed by a shearing action by the insertion of the elongated body into the patient and/or by absorption of the lubricious coating to expose the outer surface of the elongated member.

11 Claims, 13 Drawing Sheets

(51) Int. Cl.

| | |
|---|---|
| *A61M 5/145* | (2006.01) |
| *A61B 5/00* | (2006.01) |
| *A61L 29/14* | (2006.01) |
| *A61L 29/16* | (2006.01) |
| *A61M 5/158* | (2006.01) |
| *G01N 33/66* | (2006.01) |
| *C12Q 1/00* | (2006.01) |
| *A61L 31/10* | (2006.01) |
| *A61B 5/145* | (2006.01) |

(52) U.S. Cl.
CPC ............ *A61B 5/6852* (2013.01); *A61L 29/14* (2013.01); *A61L 29/148* (2013.01); *A61L 29/16* (2013.01); *A61L 31/10* (2013.01); *A61M 5/158* (2013.01); *A61M 25/0045* (2013.01); *C12Q 1/006* (2013.01); *G01N 33/66* (2013.01); *A61L 2400/10* (2013.01); *A61L 2420/06* (2013.01); *A61L 2430/00* (2013.01); *A61M 2005/1588* (2013.01); *A61M 2205/0238* (2013.01); *A61M 2230/201* (2013.01); *F04C 2270/041* (2013.01)

(56) References Cited

U.S. PATENT DOCUMENTS

| | | | |
|---|---|---|---|
| 5,621,050 A | | 4/1997 | Jarrett et al. |
| 5,653,695 A | * | 8/1997 | Hopkins ............... A61L 29/085 428/447 |
| 5,688,747 A | | 11/1997 | Khan et al. |
| 5,712,229 A | * | 1/1998 | Hopkins ............... C10M 173/02 508/202 |
| 5,736,251 A | * | 4/1998 | Pinchuk ............... A61L 27/34 427/387 |
| 5,902,631 A | * | 5/1999 | Wang ............... A61L 29/085 427/2.1 |
| 5,911,711 A | | 6/1999 | Pelkey |
| 6,102,898 A | | 8/2000 | Khan et al. |
| 6,106,889 A | | 8/2000 | Beavers et al. |
| 6,263,249 B1 | | 7/2001 | Stewart et al. |
| 6,706,025 B2 | | 3/2004 | Engelson et al. |
| 7,162,289 B2 | | 1/2007 | Shah et al. |
| 7,310,544 B2 | | 12/2007 | Brister et al. |
| 7,332,227 B2 | | 2/2008 | Hardman et al. |
| 7,552,522 B2 | | 6/2009 | Shah et al. |
| 2002/0132540 A1 | * | 9/2002 | Soerens ............... A61L 15/60 442/59 |
| 2004/0006305 A1 | * | 1/2004 | Hebert ............... A61M 25/0021 604/96.01 |
| 2004/0044404 A1 | | 3/2004 | Stucke et al. |
| 2004/0209784 A1 | * | 10/2004 | Hardman ............... A61L 29/085 508/204 |
| 2004/0236290 A1 | * | 11/2004 | Zimmermann ....... A61L 29/085 604/265 |
| 2006/0079740 A1 | * | 4/2006 | Silver ............... A61B 5/0031 600/309 |
| 2008/0086042 A1 | * | 4/2008 | Brister ............... A61B 5/14532 600/347 |
| 2008/0146990 A1 | * | 6/2008 | Jenson ............... A61B 5/03 604/28 |
| 2009/0048537 A1 | * | 2/2009 | Lydon ............... A61L 29/041 600/585 |
| 2009/0062737 A1 | | 3/2009 | Sun |
| 2009/0182408 A1 | | 7/2009 | Sydney et al. |
| 2010/0198033 A1 | | 8/2010 | Krulevitch et al. |
| 2011/0301553 A1 | * | 12/2011 | Goral ............... A01N 25/04 604/265 |

OTHER PUBLICATIONS

Database WPI, Week 201171, Thomson Scientific, London, GB; AN 2011-N06621, WPI / 2017 Clarivate Analytics (& WO 2011/129162 A1, Goodman Co. Ltd., Oct. 20, 2011.
International Preliminary Reprot on Patentability, dated Jul. 2, 2015.
Japanese Office Action dated Aug. 23, 2016 issued in a counterpart Patent Application No. 2015-549334, incl. English Translation.
European Communication Pursuant to Article 94(3) EPC which issued in corresponding Patent Application No. 12890542.9.
Database WPI Week 201171, Thomson Scientific, London GB, AN 2011-N06621 & WO 2011/129162 A1 (Goodman Co Ltd) Oct. 20, 2011, 20 pages.
Supplementary European Search Report dated Jun. 23, 2016 that issued in the corresponding Patent Application No. 12890542.9.

* cited by examiner

DEVICE AND METHOD FOR INHIBITING MOVEMENT OF A MEDICAL DEVICE IN A PATIENT

FIELD OF THE INVENTION

The present invention is directed to a device and method for facilitating insertion and inhibiting movement of a medical device with respect to the tissue at an insertion site in a patient. In particular, the invention is directed to a medical device having a lubricated portion for inserting into the patient and having a surface to limit or resist movement of the device at the insertion site after insertion.

BACKGROUND OF THE INVENTION

A cannula such as a hypodermic needle and a catheter are commonly used for delivering and withdrawing fluids from a patient. Hypodermic needles are typically coated with a suitable lubricant to assist with penetration into the skin with reduced pain to the patient.

Tissue penetration by a hypodermic needle causes several events that cause pain to the patient. The distal tip of the needle contacts the skin and stretches the skin until the tip cuts into the skin. As the shaft of needle penetrates the tissue, a sliding friction occurs between the surface of the needle and the tissue. The drag caused by the friction between the surface of the needle and the tissue contributes to the pain perceived by the patient. A lubricant on the shaft of the needle can reduce the drag force and reduce the pain perceived by the patient.

Catheters are also inserted into or through the skin of a patient to deliver or withdraw fluid to the patient. One example is an insulin delivery device for delivering a continuous or steady supply of insulin or other medication over prolonged period of time. Another example is an infusion set having a needle or catheter that is inserted through the skin at an infusion site. The infusion set typically includes a base that is attached to the surface of the skin by an adhesive. The infusion set is retained in place with the needle or catheter penetrating the skin for an extended period of time from several days to several weeks to deliver a suitable dosage of the insulin or other medication.

Diabetes requires the continuous maintenance of proper insulin dosages to the patient. To monitor the blood glucose levels in the patient, various methods and devices have been used. One device draws a sample of blood from the patient, typically by a finger stick method. A glucose sensor then measures the blood glucose level and displays the value on a suitable display.

Another type of glucose monitoring device includes a probe that is inserted into the tissue of the patient to detect glucose in body fluids such as blood. The probe includes a glucoses sensor such as a glucose binding protein, or glucose oxidase to monitor the blood glucose level on a continuous basis.

The infusion set and the glucose sensor probe can remain in the tissue for days or weeks to provide sustained delivery of the insulin and continuous monitoring of the patient's blood glucose level. The infusion set and probe are secured to the outer surface of the skin to hold the device in place and maintain proper placement and positioning of the catheter or probe in the tissue.

Prolonged usage of the catheter of the infusion set or probe causes irritation and inflammation at the site of penetration. The device must be periodically replaced at a new site and the new device must again penetrate the skin, typically through use of an insertion needle, thereby causing pain and discomfort to the patient.

While the prior devices have been generally suitable for their intended use, there is a continuing need in the industry for improved devices that reduce or minimize discomfort to the patient and irritation to the skin.

SUMMARY OF THE INVENTION

The present invention is directed to a medical device and to a method for inhibiting or limiting movement of the medical device at an insertion site in the patient. In particular, the invention is directed to a medical device adapted for insertion into a patient and having an outer surface that resists or limits movement between the device and the tissue at the insertion site.

Accordingly, one feature of the invention is to provide a medical device such as a cannula, needle, catheter, probe or biosensor adapted for insertion into the patient in a manner to inhibit, minimize or resist movement of the medical device at the insertion site after insertion and to inhibit irritation and trauma of the insertion site caused by movement of the medical device. The medical device includes a lubricated outer surface to minimize trauma to skin and/or vein during or after insertion.

One aspect of the present invention is directed to a medical device that penetrates the skin or is inserted into the patient and remains in place in the patient for an extended period of time. Examples of such medical devices include a cannula, a catheter of an insulin infusion set or insulin infusion pump or a probe of a biosensor for monitoring analytes in the patient. Another example is a probe of a blood glucose monitoring device.

The medical device of the invention has an elongated body that is inserted into the patient at an insertion site. The outer surface of the elongated body that contacts the tissue at the insertion site is modified to inhibit or limit sliding movement of the elongated body with respect to the insertion site after insertion. Limiting movement of the elongated body at the insertion site reduces irritation and inflammation of the tissue at the insertion site during extended use of the medical device.

Another feature of the invention is to provide a medical device adapted for inserting into the patient for an extended period of time where the medical device is able to move into the insertion site with reduced irritation and inflammation at the insertion site.

The features and advantages of the invention are provided by a medical device adapted for insertion into a patient and worn for an extended period of time by the patient where an outer surface of the medical device has a coefficient of friction at the interface of the insertion site to inhibit or limit movement of the medical device at the insertion site while providing sufficient lubricating properties to assist in removal of the medical device with minimal pain and discomfort to the patient.

Another feature of the invention is to provide a medical device adapted for inserting into a patient and to be worn by the patient for an extended period of time where the device has a lubricious coating to assist in insertion of the medical device and a contact surface for contacting the insertion site after insertion into the patient. The contact surface of the medical device has a coefficient of friction higher than the lubricious coating to inhibit prolonged movement of the medical device between the medical device and tissue interface at the insertion site during wear after insertion.

The various advantages and features of the invention are provided by a medical device having an elongated body adapted for inserting into the patient, where the elongated body includes a lubricious coating to assist penetration an insertion of the elongated body into an insertion site. The lubricious coating can be removed by a shearing action by the insertion and drag force of the elongated body to expose an outer surface of the elongated body. The outer surface of the elongated body has a coefficient of friction that is higher than a coefficient of friction of the lubricious coating to resist or limit movement between the elongated body and the insertion site to reduce irritation and inflammation at the insertion site.

The features of the invention are provided by a biosensor probe having an outer surface and a lubricious coating to assist insertion of the probe into a patient. The lubricious coating can be removed upon insertion into the patient. Alternatively or in addition, the lubricious coating is removed after insertion into the patient to expose the outer surface of the probe. The lubricious coating can be soluble or bioabsorbable by body fluids at the infusion site. The outer surface of the probe can have a textured or roughened surface or an inner coating layer to provide the probe with a coefficient of friction sufficient to resist sliding at an interface between the probe and the tissue at the insertion site. The inner coating can be at least partially degradable to produce a surface having a texture with a coefficient of friction to inhibit sliding movement between the probe and the tissue at the insertion site.

Another aspect of the invention is to provide a medical device for insertion into a patient where the outer surface of the medical device has a tissue growth promoting component and a coating of a lubricious material. The tissue growth promoting component promotes tissue growth at the insertion site of the device to inhibit movement of the device at the insertion site after deployment.

These and other aspects of the invention are attained by providing a medical device comprising an elongated body having an outer surface, a distal end and a proximal end. The distal end of the device is adapted for inserting into the skin of a patient. An outer lubricious coating is applied at least at the distal end on the outer surface to assist insertion in the skin by the elongated body. The outer surface of the elongated body has at least a portion thereof with a coefficient of friction higher than the lubricious coating to inhibit movement of the elongated body with respect to the skin after insertion and to inhibit irritation of the skin.

The various features of the invention are further attained by providing a biosensor probe for penetrating and inserting in the skin of a patient. The biosensor probe comprises an elongated body having a sensor for detecting an analyte, a proximal end, a distal end and an outer surface. A lubricious coating is applied at least to the distal end of the elongated body to assist penetration of and insertion in the skin of the patient. The elongated body has at least one contact area with a surface adapted for providing a coefficient of friction higher than a coefficient of friction of the lubricious coating to resist movement of the cannula relative to the skin after insertion.

The advantages and features of the invention are also attained by providing a method of inhibiting movement of a medical device inserted through the skin of a patient. The method comprises the steps of providing the medical device with an elongated body having a distal end, a proximal end, an outer surface and a lubricious coating on the outer surface at least at the distal end. The outer surface of the elongated body has a coefficient of friction greater than a coefficient of friction of the lubricious coating. The elongated body is inserted in the skin of the patient where the lubricious coating assists insertion of the elongated body in the skin and where the outer surface of the elongated body contacts the skin to inhibit or minimize movement of the elongated body with respect to the skin after insertion.

The various objects, advantages and salient features of the invention will become apparent from the following detailed description of the invention, which in conjunction with the drawings, disclose various embodiments of the invention.

BRIEF DESCRIPTION OF THE DRAWINGS

The following is a brief description of the drawings, in which.

DETAILED DESCRIPTION OF THE INVENTION

Figure 1:
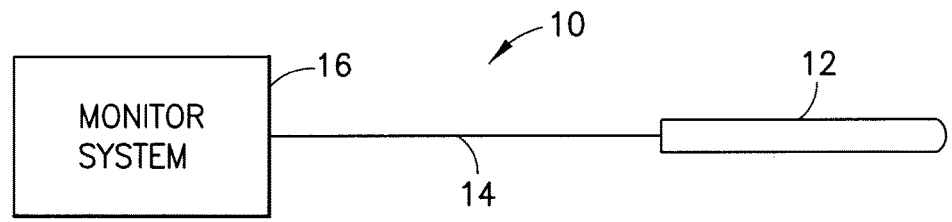
FIG. 1 is a schematic view of the probe sensor in one embodiment of the invention.

The present invention is directed to a medical device that can be inserted into the tissue of a patient. The invention is particularly directed to a medical device adapted for insertion into the tissue of a patient for extended periods of time with reduced irritation and inflammation at the insertion site. In the various embodiments described herein, the medical device can be a sensor probe for sensing and measuring an analyte concentration in body fluids. One particular example is a glucose sensor probe for the continuous monitoring of glucose blood levels in a patient. In other embodiments, the medical device can be an insulin infusion set having a cannula, a needle or catheter for delivering insulin or other medicaments to the patient. It will be understood that the cannula and probe are intended to be exemplary and that the invention is suitable for other medical devices that are adapted for penetrating the skin of a patient and are adapted to be retained in the tissue of the patient for extended periods of time.

A cannula, needle or probe is adapted to be inserted into the tissue of a patient and remain in the tissue for extended periods of time depending on the device and its intended use. For example, a glucose sensor probe of a glucose monitor is generally intended to remain in the insertion site for at least a day to more than one week. The medical device can be inserted intravenously, cutaneously or subcutaneously depending on the structure and intended use of the medical device.

The longer the time the probe or cannula remains in the insertion site in the tissue, the greater the risk of irritation and inflammation of the tissue at the insertion site. It has been found that during normal use and movement by a patient, the probe or cannula will move slightly in an inward and outward direction causing irritation. Such movement is generally referred to as "pistoning" which causes irritation and inflammation at the insertion site. The movement of the probe or cannula relative to the insertion site creates a drag or friction causing irritation and inflammation. The irritation of the tissue at the insertion site typically leads to an inflammatory response at the insertion site. In a probe having a glucose sensor, the resulting inflammatory response will often compromise the sensor accuracy and responsiveness.

The medical device of the present invention can be a probe, cannula or needle that has a suitable coating to provide easy insertion into the tissue to minimize trauma and discomfort during insertion and has a surface that comes into contact with the tissue after insertion that minimizes movement between the device and the tissue interface. The invention is particularly directed to a medical device that has a lubricious coating to provide the necessary lubricity to facilitate penetration and/or insertion into the tissue of the patient while providing a surface having a reduced lubricity after insertion to reduce or limit movement of the device relative to the tissue at the insertion site. The lubricity is selected to reduce the pistoning effect when worn by the patient for extended periods of time. Examples of suitable analyte sensors or probes are disclosed in U.S. Pat. Nos. 7,310,544 and 7,713,574, which are hereby incorporated by reference in their entirety.

In one embodiment of the invention, the medical device is a probe having an immobilized sensor for sensing an analyte that can be inserted and immobilized in the tissue of a patient. The probe is adapted for insertion into the patient and can be worn for an extended period of time. A probe or other device that is not lubricated can require a high insertion force to break the skin and can cause high friction forces against the tissue to continue inserting the probe through the skin resulting in end user discomfort. Unlubricated probes can cause discomfort to the patient during insertion and can cause local inflammation, repeated aggravation and injury. The microscopic movement of the probe relative to the tissue occurs as a result of the normal use and wearing of the probe. The movement of the probe can cause discomfort at the insertion site and local accumulation of blood components to alleviate the inflammation. The accumulation of the blood components can hinder the performance of the sensor and particularly a blood glucose sensor. The irritation and inflammation also can result in reduced wearing time by the patient and a greater need to relocate the probe to different sites.

Referring to the drawings, various exemplary embodiments are shown. In the embodiment shown in FIG. 1, the medical device 10 includes a probe 12 adapted for inserting in the tissue of a patient as known in the art. The probe 12 in the embodiment illustrated includes a glucose sensor capable of detecting glucose levels in the body fluid. The probe is connected by a wire or optical fiber 14 to a glucose monitoring system 16. The glucose monitoring system 16 as known in the art receives signals from the probe 12 and calculates a blood glucose level which can be displayed or recorded by the system. Examples of such glucose monitoring systems are known in the art.

Figure 2:
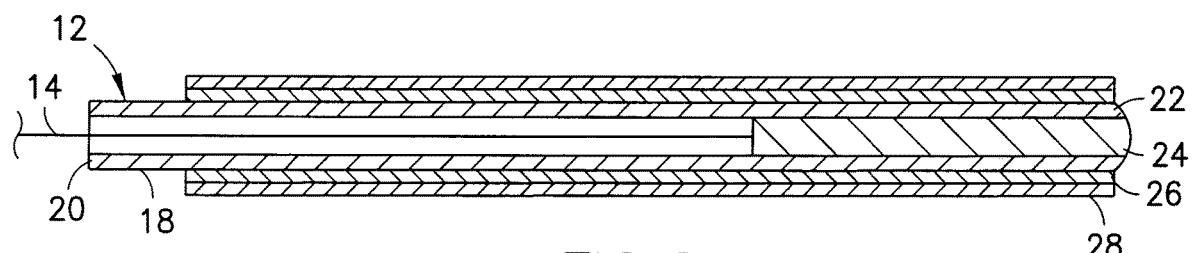
FIG. 2 is a cross-sectional view of the probe.

Referring to FIG. 2, the probe 12 in one embodiment of the invention includes an elongated body 18 which can be rigid or flexible. A proximal end 20 is connected to the wire 14. A distal end 22 supports the glucose sensing unit 24. The glucose sensing unit 24 in one embodiment of the invention can include a glucose binding protein, or a glucose oxidase sensor. The probe has a length and a diameter suitable for inserting in the tissue site and can be inserted into the patient by procedures, locations and depths as known in the art. The medical device can have a sharpened tip, insertion needle or other insertion device as known in the art for inserting and positioning a probe, cannula or other medical device in a patient and at a suitable depth of penetration depending on the intended use of the medical device. Examples of suitable glucose binding proteins and glucose monitoring probes are disclosed in U.S. Pat. No. 6,277,627 to Hellinga, U.S. Pat. No. 7,064,103 to Pitner et al., and U.S. Pat. No. 7,326,538 to Pitner et al., and U.S. Patent Publication No. 2008/0275318 to Lastovich et al., which are hereby incorporated by reference in their entirety.

In the embodiment of FIG. 2, the probe includes an inner coating 26 and an outer lubricious coating 28 applied over the inner coating 26. The outer coating 28 forms a lubricated coating to assist in penetration, insertion and positioning of the probe through the insertion site 32 in the tissue 30 of a patient. The lubricant can be a suitable lubricant known in the art. One example of a suitable lubricant is a polydimethyl siloxane. The inner coating 26 is a polymeric material bonded to the outer surface of the probe 18. The probe surface 18 is generally made of a polymeric material such as a polyurethane, silicone resin. The inner coating 26 is applied to the outer surface of the probe around the entire outer surface. An adhesion promoter can be incorporated into the polymeric material as needed.

In one embodiment shown in FIG. 2, the inner coating 26 extends from the distal end 22 of the probe 18 along a length of a contact area sufficient to contact the tissue at the insertion site after insertion and positioning in the patient.

In one embodiment of the invention, the outer lubricious coating 28 is a relatively soft material that can be wiped from the inner coating 26 and the probe upon insertion into the tissue.

Figure 3:
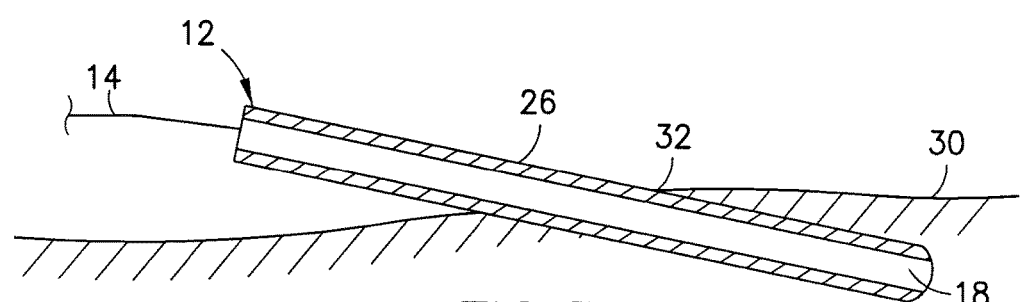
FIG. 3 is a partial view of the probe inserted into a patient.

Referring to FIG. 3, the probe 12 is inserted into the tissue 30 of a patient at an insertion site 32. The outer lubricious coating 28 contacts the tissue at the insertion site 32 during insertion to assist in the penetration of the probe 12 and reduce frictional drag forces between the probe 12 and the tissue 30. In the embodiment shown in FIG. 3, the lubricious coating 28 is completely or partially removed by the insertion into the tissue at the insertion site 32 to expose the inner coating 26. The inner coating 26 has a lubricity that is less than the outer lubricious coating and coefficient of friction greater than a coefficient of friction of the outer lubricious coating 28. The inner coating 26 when exposed to the tissue forms an outer surface with a sufficient static and/or dynamic coefficient of friction to minimize, resist or limit movement of the probe with respect to the tissue and reduce the pistoning effect. By providing the inner coating with a sufficient static and/or dynamic coefficient of friction, movement of the tissue by the patient allows the probe to move together with the tissue at the insertion site 32 and limit sliding movement of the probe with respect to the tissue. In a similar manner, small movement of the probe enables the tissue at the insertion site 32 to move with the small movements of the probe. By reducing or preventing the sliding motion in or out of the tissue and relative movement of the probe with respect to the tissue at the insertion site 32, inflammation and irritation of the tissue at the insertion site can be reduced.

The outer lubricious coating 28 can be a soft or low viscosity lubricant. The lubricious coating is preferably sufficiently viscous to remain on the outer surface of the inner coating 26 and to provide sufficient lubrication of the probe during insertion into the tissue site. The viscosity of the lubricant in this embodiment is preferably sufficiently low that the drag forces during insertion remove at least a portion of the lubricious coating to expose the inner coating 26.

The lubricant used to form the outer lubricious coating can be any suitable lubricant as known in the art that is capable of providing the necessary lubricity for initial penetration and insertion of the medical device into the tissue. One example of a lubricant that can be removed or partially removed from the medical device such as a probe or cannula by the drag force or friction with the tissue at the insertion site is an uncrosslinked lubricant such as a water based lubricant. A suitable water based lubricant can be a water based silicone polymer lubricant having a lubricity sufficient to lubricate the surface of the medical device to allow ease of insertion with reduced pain and discomfort to the patient. The water based silicone lubricant can be easily coated onto the surface of the medical device and removed by the insertion drag force. Alternatively or in addition, the water based lubricant can be removed completely or partially after insertion into the tissue by dissolving or dispersing in the body fluids to expose the surface of the medical device having the coefficient of friction necessary to limit the sliding movement of the medical device with respect to the insertion site during normal use and wear of the medical device. One example of a silicone surfactant is a polydimethyl siloxane having a molecular weight of 20,000 and a viscosity of 1700 centistokes and is soluble in water. A suitable water based silicone lubricant is disclosed in U.S. Pat. No. 4,664,657 to Williamitis et al. and U.S. Pat. No. 5,688,747 to Khan et al. which is hereby incorporated by reference in its entirety.

The inner coating 26 can be a polymeric coating that can be permanently fixed to the outer surface of the probe. The inner coating 26 can also be made from a biodegradable or bioabsorbable polymer such as a polylactic acid which can degrade and be absorbed at the tissue site. The degradation at the surface of the inner coating 26 can produce a textured or roughened surface at the tissue site caused by the body fluids to provide the necessary coefficient of friction to prevent slippage or movement of the probe relative to the insertion site. In various embodiments of the invention, the inner coating 26 can include various active agents or pharmaceutical agents such as a tissue growth agent to promote tissue growth at the insertion site and to attach the tissue to the probe, thereby preventing or minimizing relative movement between the probe and the insertion site.

The inner coating applied to the surface of the medical device between the surface of the medical device and the lubricant formulated a biodegradable or bioabsorbable polymer coating. In one embodiment of the invention, the inner coating is able to at least partially degrade, dissolve or disperse in the body fluids from the insertion site to produce a surface texture on the coating and/or the medical device that provides the desired coefficient of friction to inhibit the excessive movement of the medical device at the insertion site by normal movement by the patient. The biodegradable coating can be tailored to erode at a predetermined rate to provide a surface texture of the coating within a selected period of time after insertion and exposure to the body fluids. The textured surface of the inner coating preferably has a coefficient of friction greater than the outer lubricant used for insertion of the medical device. Examples of biodegradable polymers include polylactic acid polymers, polyanhydride polymers, hydroxybutyrate polymers, polyvinyl alcohol polymers, polycaprolactone polymers, starch derivatives and cellulose derivatives.

In one embodiment, the inner coating that comes into contact with the tissue at the insertion site can include a growth promoting substance such as growth factor in an amount sufficient to promote tissue growth at the insertion site. The growth promoting substance is preferably able to promote tissue growth at the interface of the medical device and tissue provide the necessary drag force by the tissue to reduce the movement between the medical device and the tissue at the insertion site.

The inner coating and/or the lubricant coating can also contain other bioactive agents such as an antimicrobial agent or antibacterial agent. Other bioactive agents include anti-inflammatory agents, an enzyme, a hormone, a therapeutic drug, a vitamin, an antibody, antigen, nucleic acid, a protein or peptide, a polysaccharide or heparine.

Figure 4:
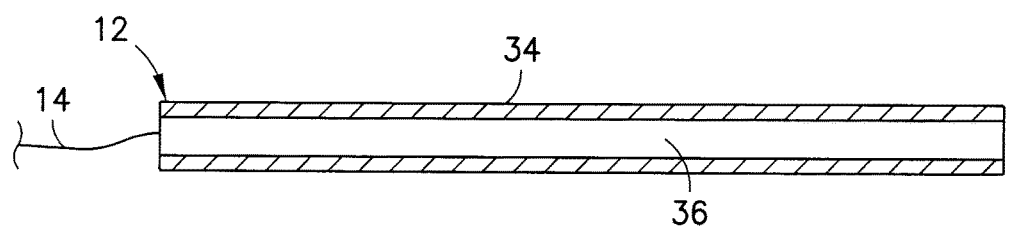
FIG. 4 is a partial cross-sectional view showing the probe with a single coating.

In another embodiment of the invention shown in FIG. 4, the probe 12 includes a single coating 34 on the outer surface of the elongated body 36 of the probe. The coating 34 has a coefficient of friction to enable easy insertion of the probe into the insertion site in the tissue in the manner shown in FIG. 3. The lubricious coating 34 can be biodegradable or bioabsorbable as in the previous embodiment. In this embodiment, the probe is inserted into the tissue at the insertion site where the body fluids dissolve or decompose the lubricious coating 34 after insertion. The lubricious coating 34 dissolves or degrades to expose the outer surface of the probe 36.

In this embodiment, the outer surface of the probe has a coefficient of friction greater than the coefficient of friction of the lubricious coating. As the lubricious coating 34 is dissolved or absorbed, the outer surface of the probe is exposed and comes into contact with the tissue at the insertion site. The surface of the probe 36 having a coefficient of friction greater than the coefficient of friction of the lubricious coating provides sufficient frictional drag force between the probe and the tissue at the insertion site to inhibit relative movement between the probe and the insertion site. In this embodiment, the outer surface of the probe has a textured or roughened surface to provide the necessary coefficient of friction. The textured outer surface can be obtained by mechanical means or by a chemical means. The textured surface can be formed by raised portions on a micron or submicron scale. The height of the raised portions can range from about 1 µm to 100 µm in one embodiment. The shape and height of the raised portions forming the textured surface can vary depending on the use and material of the probe.

Figure 5:
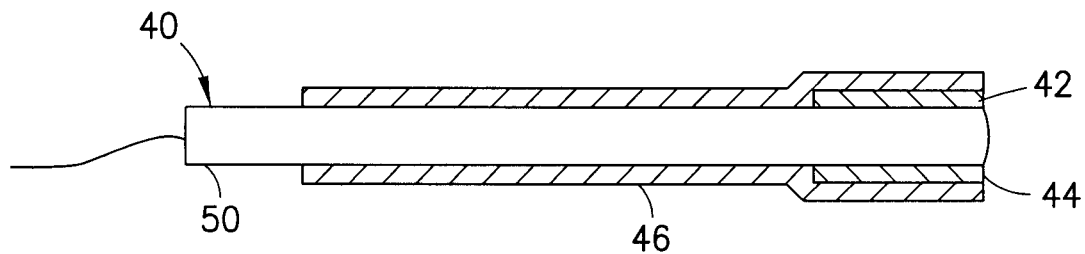
FIG. 5 is a cross-sectional view of the probe showing a coated tip and an overcoat layer.

In another embodiment shown in FIG. 5, the medical device is a probe 40 having a distal end forming a tip 42 coated with a lubricant 44 such as a crosslinked polysiloxane lubricant. In this embodiment, only tip 42 is coated with the crosslinked lubricant. The medical device is then coated with an outer layer 46 of an uncrosslinked lubricant such as a water dispersible or water based silicone lubricant. The outer layer 46 extends over the inner lubricant coating 44 at the tip 42 and extends from the distal end 42 toward the proximal end 50 a distance sufficient to cover the area that will come in contact with the tissue when positioned in the insertion site. The outer lubricant layer 46 provides the necessary lubricity to assist in the insertion of the medical device into the tissue at the insertion site. The outer lubricant layer 46 can be partially or substantially wiped from the surface of the medical device upon insertion as in the previous embodiment. Alternatively, the outer lubricant 46 can be tailored to dissolve or disperse in the body fluids at the insertion site to form a textured surface for contacting the tissue at the insertion site or to expose the surface of the medical device. The resulting surface preferably has a coefficient of friction greater than the initial coefficient of the original lubricant coating in the contact area of the medical device to inhibit movement and friction at the insertion site while reducing the lubricity to prevent excessive movement between the medical device and the tissue. The distal end of the medical device has the crosslinked lubricant covering a sufficient area of the device to allow some limited movement while being worn by the patient to minimize irritation at the insertion site while allowing removal of the device with minimal discomfort.

A crosslinked lubricant is particularly suitable for use on the medical device when the lubricant in intended to remain on the surfaces of the medical device after insertion into the tissue. One such crosslinked lubricant can be formed from a mixture of polymers where at least one of the polymers is capable of crosslinking in the presence of an activator. An example of a crosslinked lubricant is formed from a mixture of a high viscosity silicone polymer that is dissolved or diluted in a low viscosity siloxane polymer which acts as a carrier and reactive silicone polymer which is capable of crosslinking to form a crosslinked polymer network. Typically, the crosslinkable polymer is an ethylenically unsaturated component. An adhesion promoter can be added if needed to promote adhesion of the lubricant coating to the surface of the medical device. The mixture of the silicone polymers can be applied to the surface of the medical device by spraying, dipping or other methods known in the art and cured in place. The polymer mixture can be cured by a photo-initiator to promote free radical crosslinking by exposure to UV light. Suitable crosslinking agents include ketones such as benzyl and benzoin and acyloins and acryoin esters. The thickness of the coatings is generally in the range of about 50 to 500 microns. One example of a suitable crosslinked lubricant is disclosed in U.S. Pat. Nos. 7,332,227, 6,102,898 and 5,911,711, which are hereby incorporated by reference in their entirety.

Figure 6:
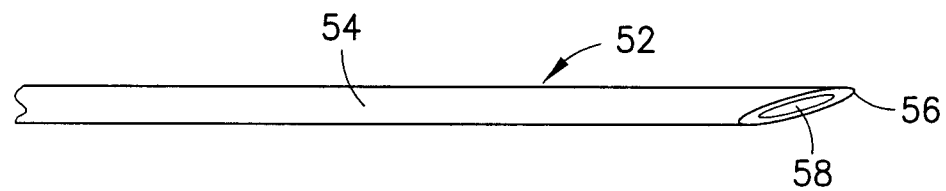
FIG. 6 is a side view of a cannula having a lubricious coating.
Figure 7:
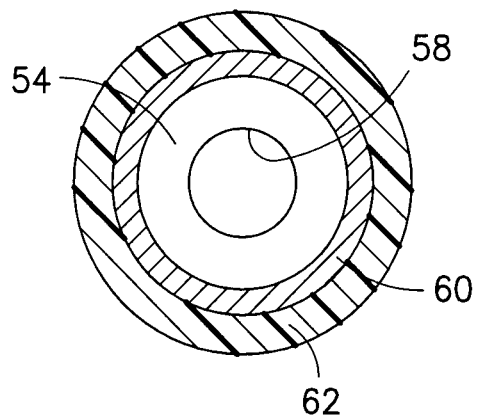
FIG. 7 is a cross-sectional view of the cannula showing the layers of the coating.

FIGS. 6 and 7 show another embodiment of the invention where the medical device is a cannula 52 having a cylindrical body 54, a pointed sharp tip 56, and bore 58 for delivering fluid or removing fluid from the patient. As shown in FIG. 7, the cannula has an inner coating 60 of a first lubricant and a second outer coating 62 of a second lubricant. In this embodiment, the inner coating 60 is a polymeric coating having a lubricity less than the lubricity of the outer coating. The outer lubricant coating 62 can be an uncrosslinked silicone polymer having a lubricity sufficient to enable efficient insertion and penetration of the cannula. The outer lubricant coating 62 in this embodiment is removed or partially removed upon insertion into the tissue to expose the surface of the inner coating 60 and the cannula 52 at the tissue interface and provide the necessary friction to inhibit movement between the cannula and the tissue. The inner lubricant at the tip of the cannula can be a crosslinked silicone polymer that remains intact on the tip which allows some movement of the tip with reduced irritation of the tissue and provides sufficient lubrication for extraction of the cannula with minimum pain to the patient.

The following examples were carried out to simulate the behavior of movement or pistoning of a medical device at an insertion site.

Example 1

A 31 gauge by 5 mm needle was used to demonstrate the movement and effect of a medical device inserted in the tissue of a patient. In this example, a needle with no lubrication was used. The needle was used to penetrate a proprietary substrate to simulate tissue of a patient. The needle penetrated the substrate once followed by holding the needle in place for a fixed duration. Thereafter, a slight pulling out and pushing in action was applied to the needle. The pulling out and pushing in action occurred over a small fraction of the total insertion depth and at a slow speed compared to the speed of the initial insertion. The movement and speed of the pulling out and pushing in action on the needle was carried out to simulate normal movement of a probe or catheter in the tissue of a patient over an extended period of time. The pulling out and pushing in motion was used in the testing to simulate what is expected to be observed in a real life use such as a body sensor being attached to the surface of the skin of a patient by an adhesive but that does not prevent small changes in body or skin motion around the insertion site. The pulling out and pushing in action was conducted multiple times to simulate the wear time of an actual medical device. The force values generated in this example are provided for comparative values between the examples and do not necessarily correspond to absolute terms.

Figure 8A:
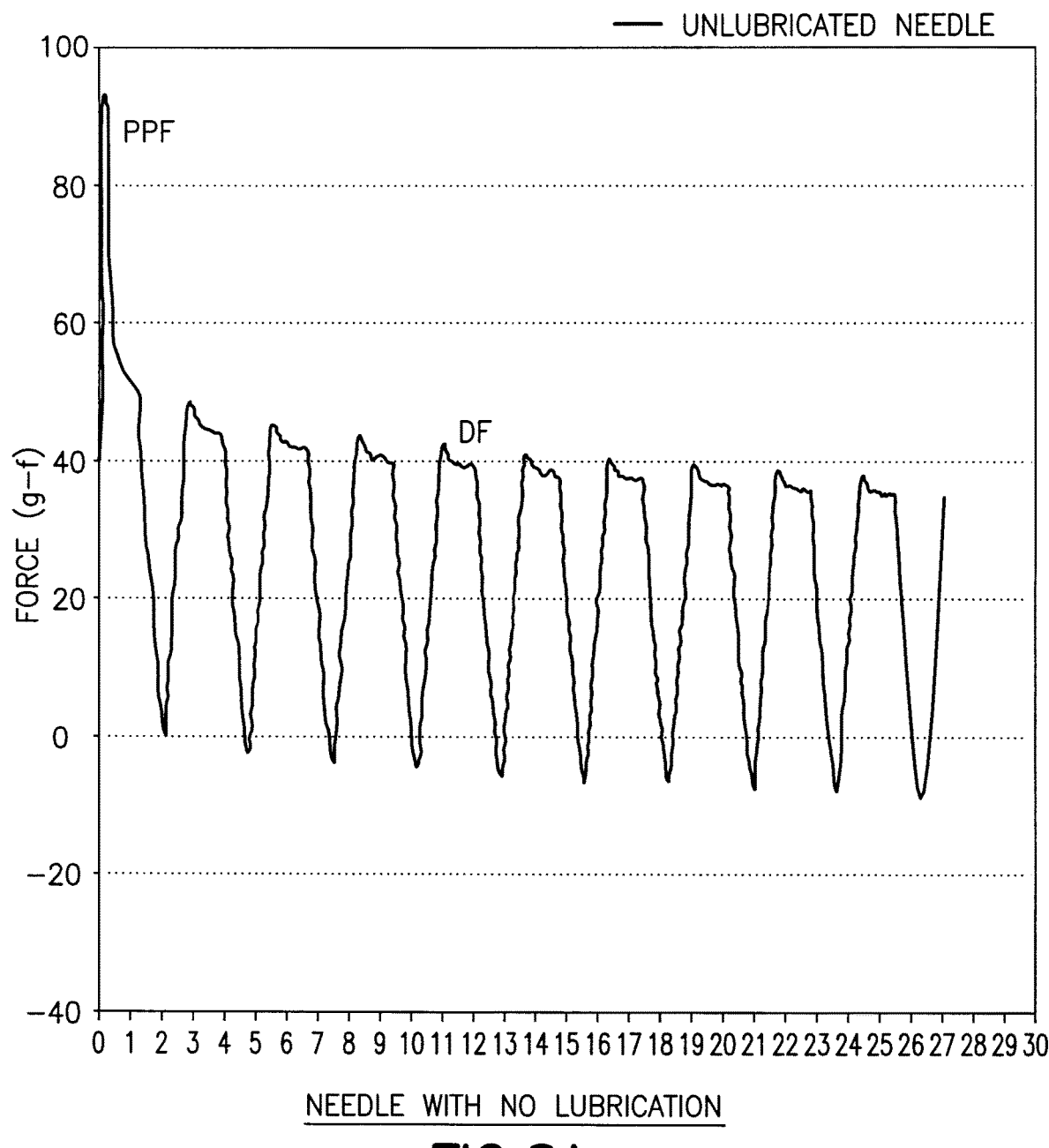
FIGS. 8A and 8B are graphs showing the force of an uncoated needle of Example 1.
Figure 8B:
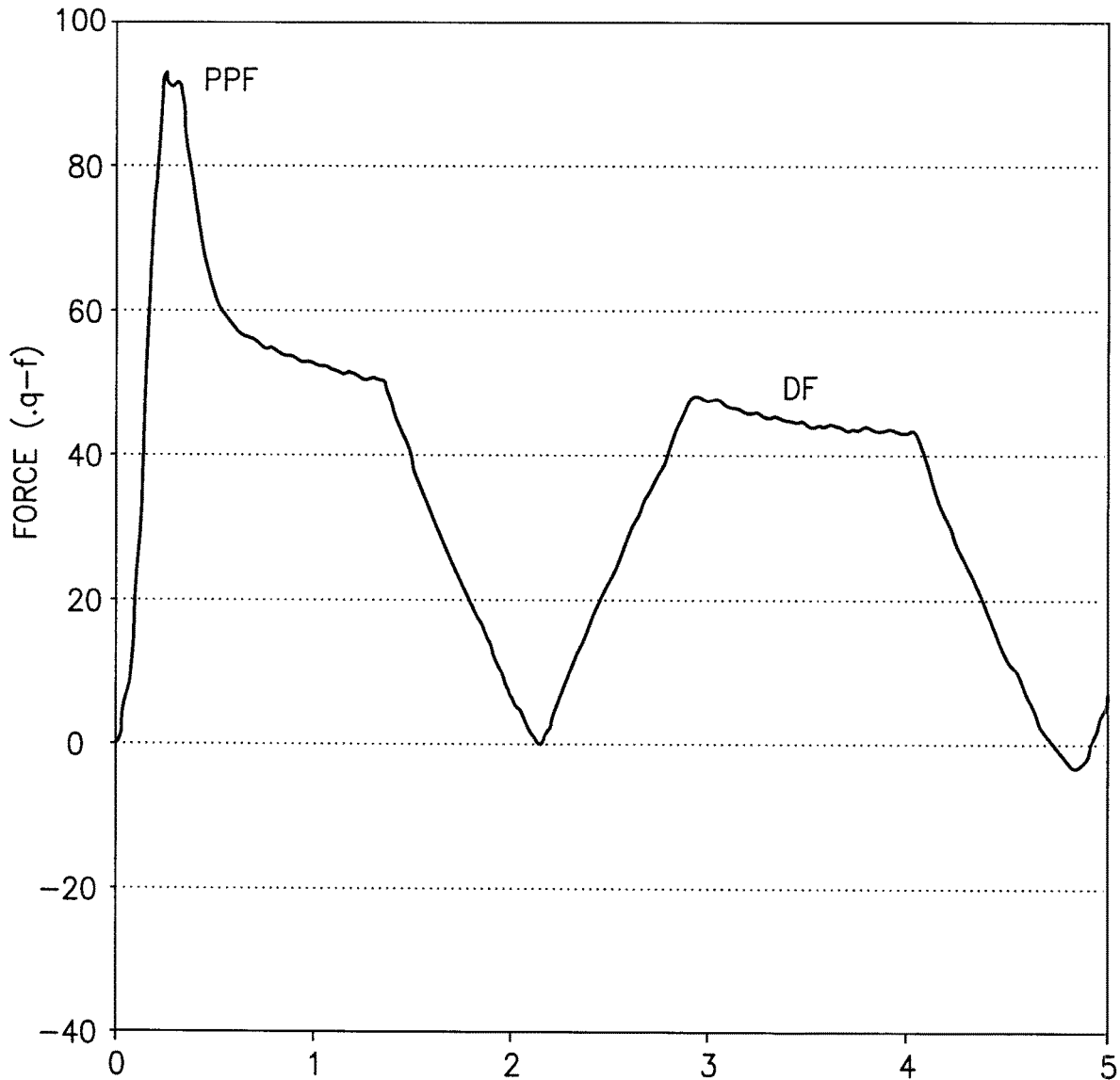

FIG. 8A is a plot of the force over multiple cycles. FIG. 8B is a plot of the force required to insert the needle and the force applied to the pulling out and pushing in motion over multiple cycles and a magnified plot showing the force over 5 cycles. In FIG. 8, PPF refers to the peak penetration force reflecting the initial high force of insertion of the needle into the substrate followed by the high friction force or drag force (DF) during insertion of the needle. The subsequent pulling out and pushing in of the needle show a similar high drag force (DF) between the needle and the insertion site of the substrate.

Example 2

Figure 9A:
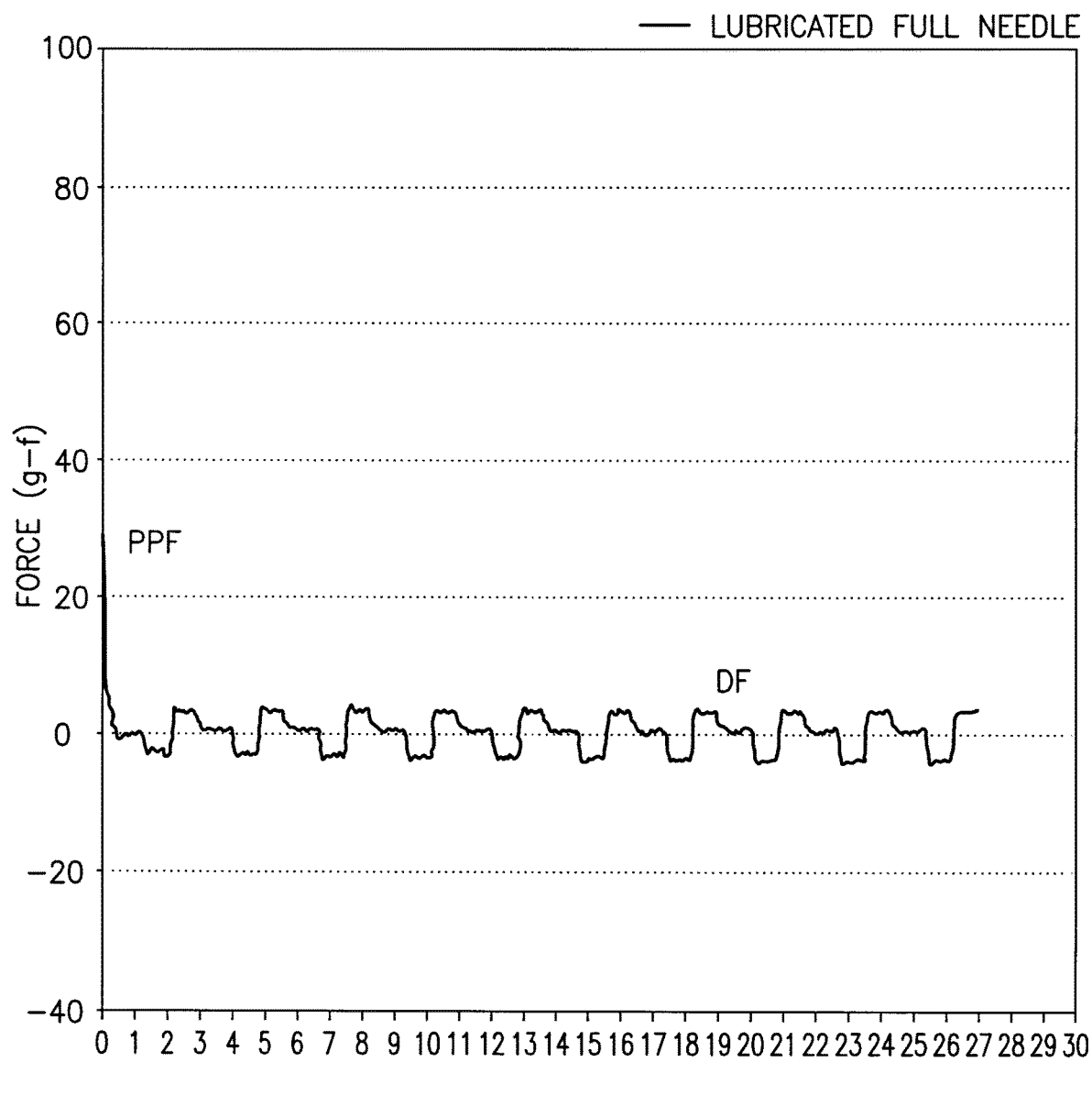
FIGS. 9A and 9B are graphs showing the force of a needle coated with a crosslinked lubricant of Example 2.
Figure 9B:
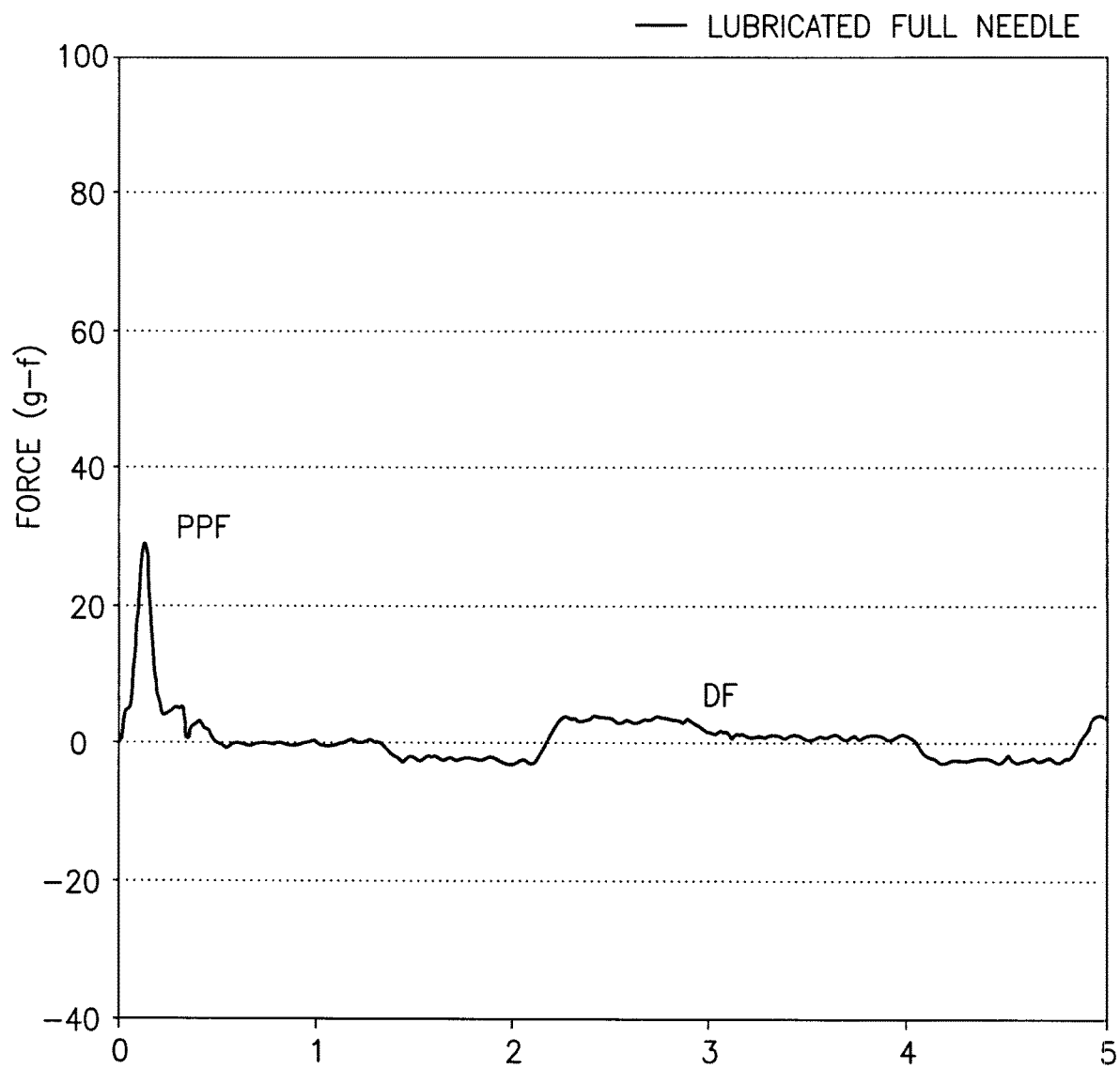

In this example, a 31 gauge by 5 mm needle was used as in Example 1 which was coated with a crosslinked lubricant composition. The lubricant coated needle was inserted into the substrate. As shown in FIG. 9A and FIG. 9B, the initial peak penetration force is reduced, relative to that shown in FIG. 8A resulting in an easier insertion into the substrate. The drag force is also significantly reduced, relative to that shown in FIG. 8A and FIG. 8B suggesting that the needle is free to move when compared to the drag force of Example 1. The reduced drag force shown in the Figures show the ease at which the needle can move in the substrate as a result of slight changes in movement by a patient simulated by the substrate. The ease of movement of the needle may be detrimental to the performance of a sensor since it might actively promote pistoning. The Figures also show the drag force profile and a stick slip phenomenon that causes the force to vary during the pulling out and pushing in of the needle in the substrate.

Example 3

Figure 10A:
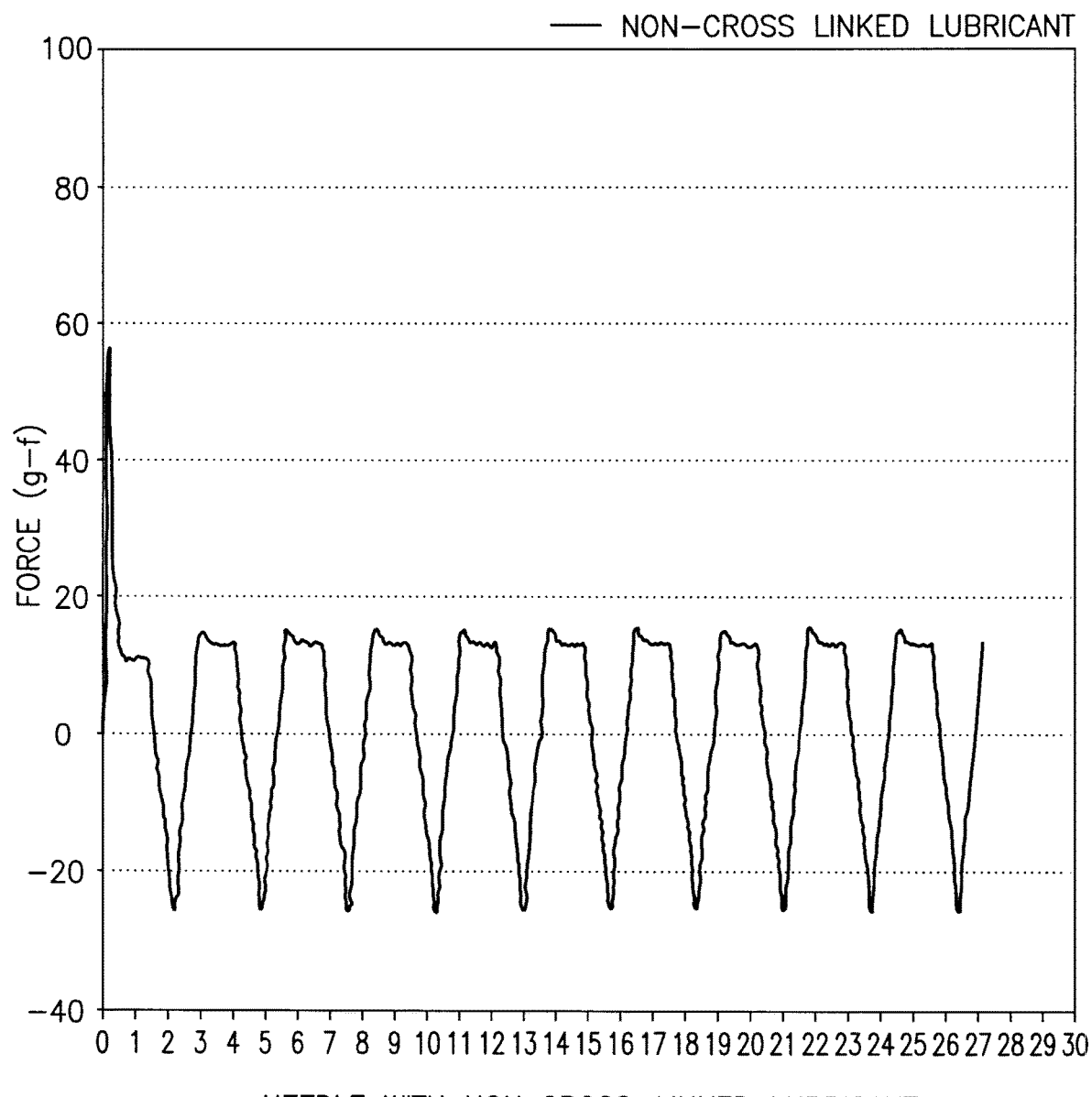
FIGS. 10A and 10B are graphs showing the force of a needle coated with an uncrosslinked lubricant of Example 3.
Figure 10B:
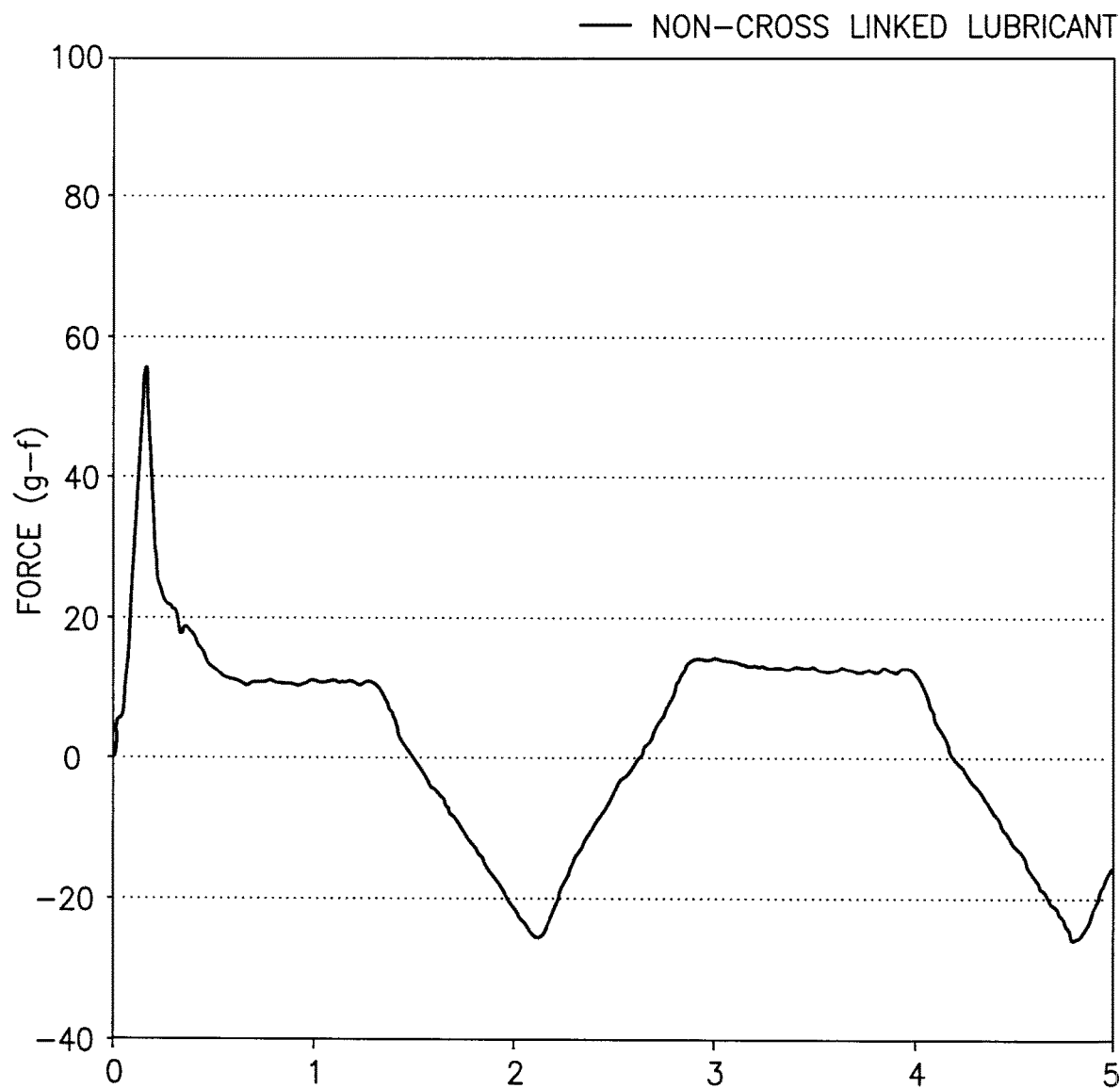

In this example, a 31 gauge by 5 mm needle was coated with a non-curing lubricant that does not form a crosslinked network and does not bond to the surface of the needle. FIG. 10A and FIG. 10B demonstrates that the lubricant provides a reduced peak penetration force and a drag force compared to an unlubricated needle relative to that shown in FIG. 9A and FIG. 9B. FIGS. 10A and 10B when compared with FIGS. 9A and 9B of Example 2 indicate that the uncrosslinked lubricant has an increased peak penetration force and drag force when compared to the needle coated with a crosslinked lubricant of Example 2. This example proposes an intermediate configuration where the needle pull out and push in movement is not too hindered and not too enabled by the highly lubricious coating of Example 2.

Example 4

Figure 11A:
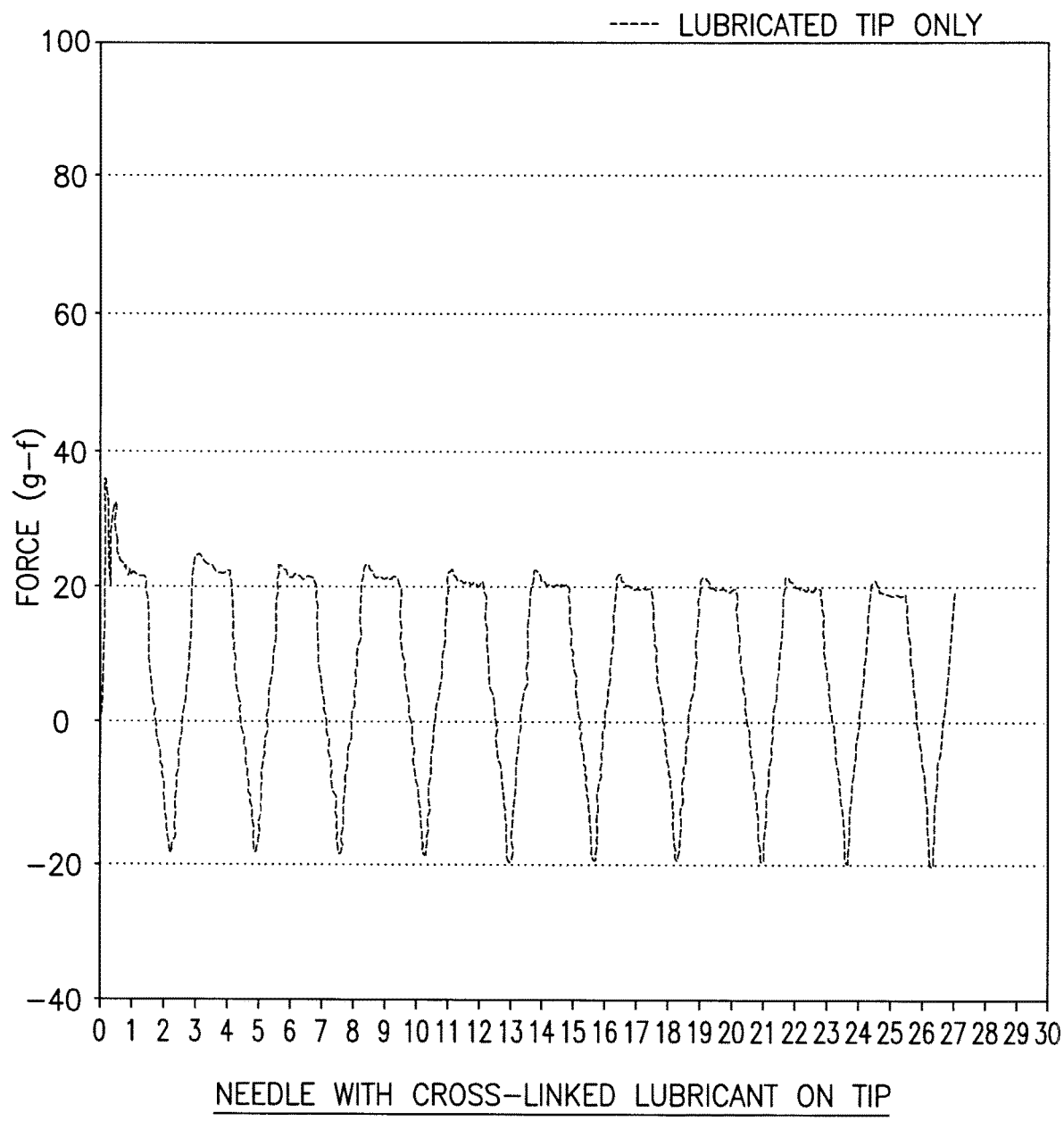
FIGS. 11A and 11B are graphs showing the force of a needle with a crosslinked lubricant on the tip of Example 4.
Figure 11B:
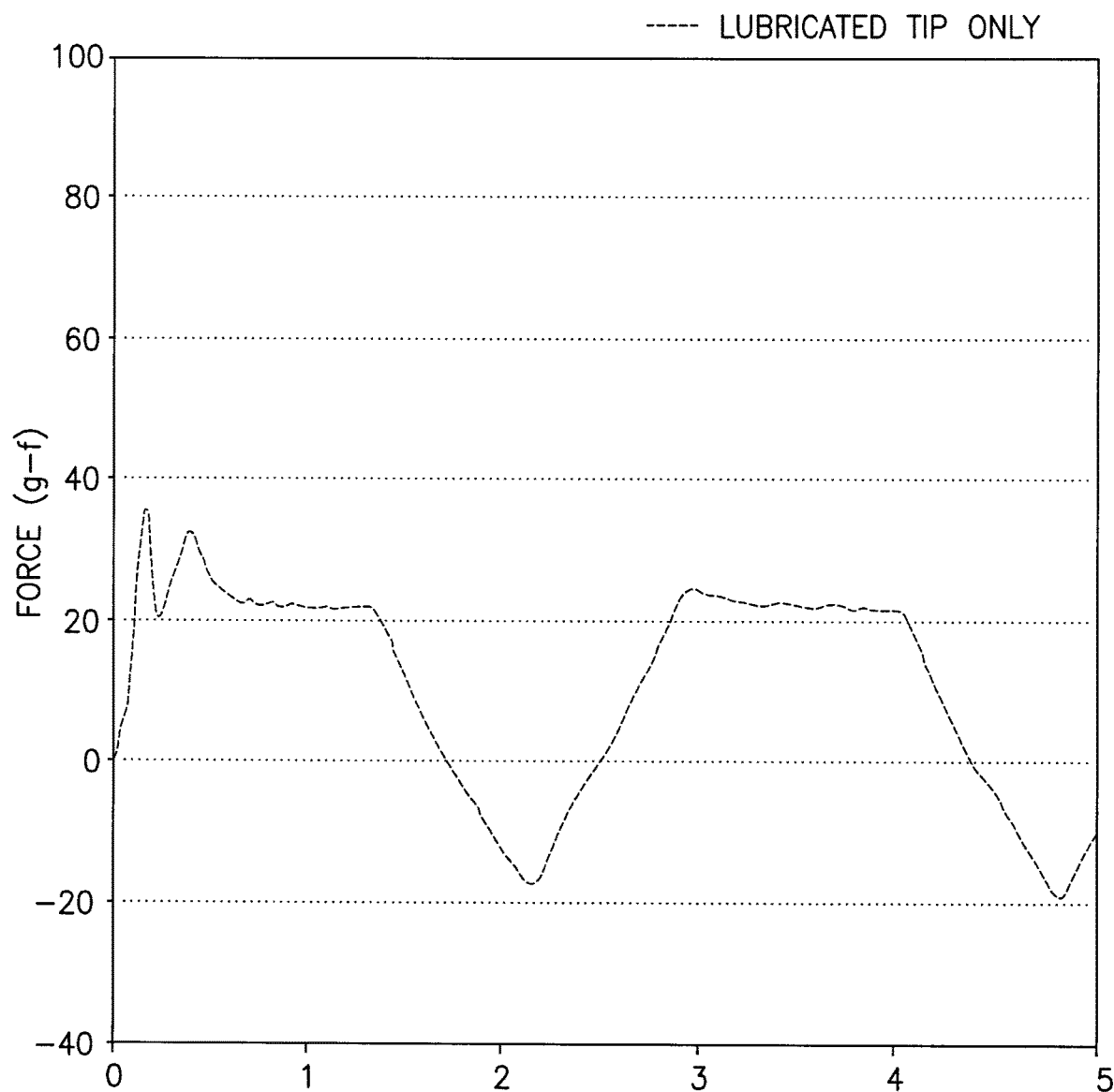

In this example, a 31 gauge by 5 mm needle as in Example 1 was used where only the tip of the needle was coated with a crosslinked lubricant. As shown in FIG. 11A and FIG. 11B, the lubricated tip provides a reduced peak penetration force relative to FIGS. 9A and 9B but maintains a relatively high drag force.

Example 5

Figure 12A:
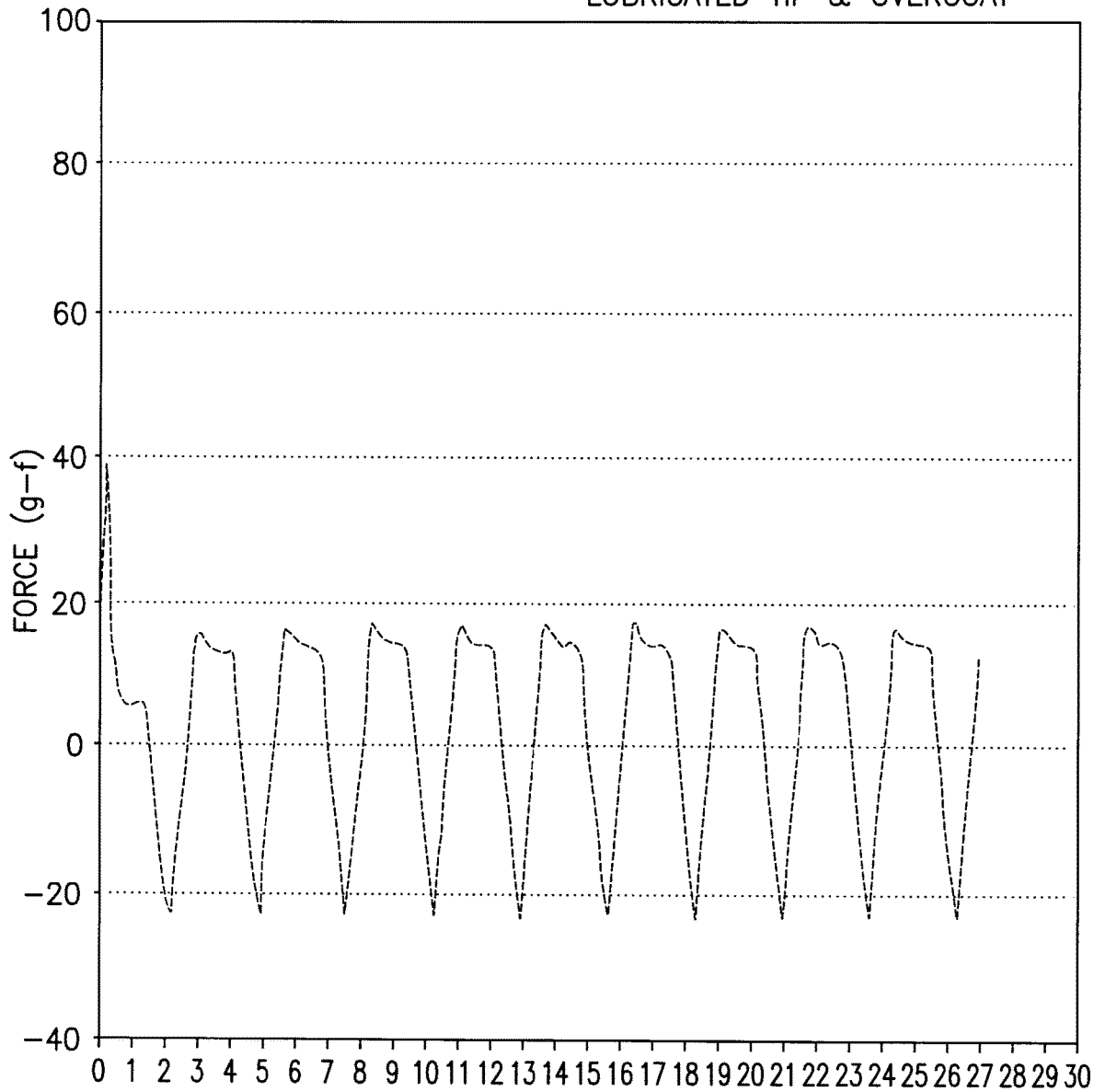
FIGS. 12A and 12B are graphs of a needle with a crosslinked lubricant on the tip and an overcoat of an uncrosslinked lubricant of Example 5.
Figure 12B:
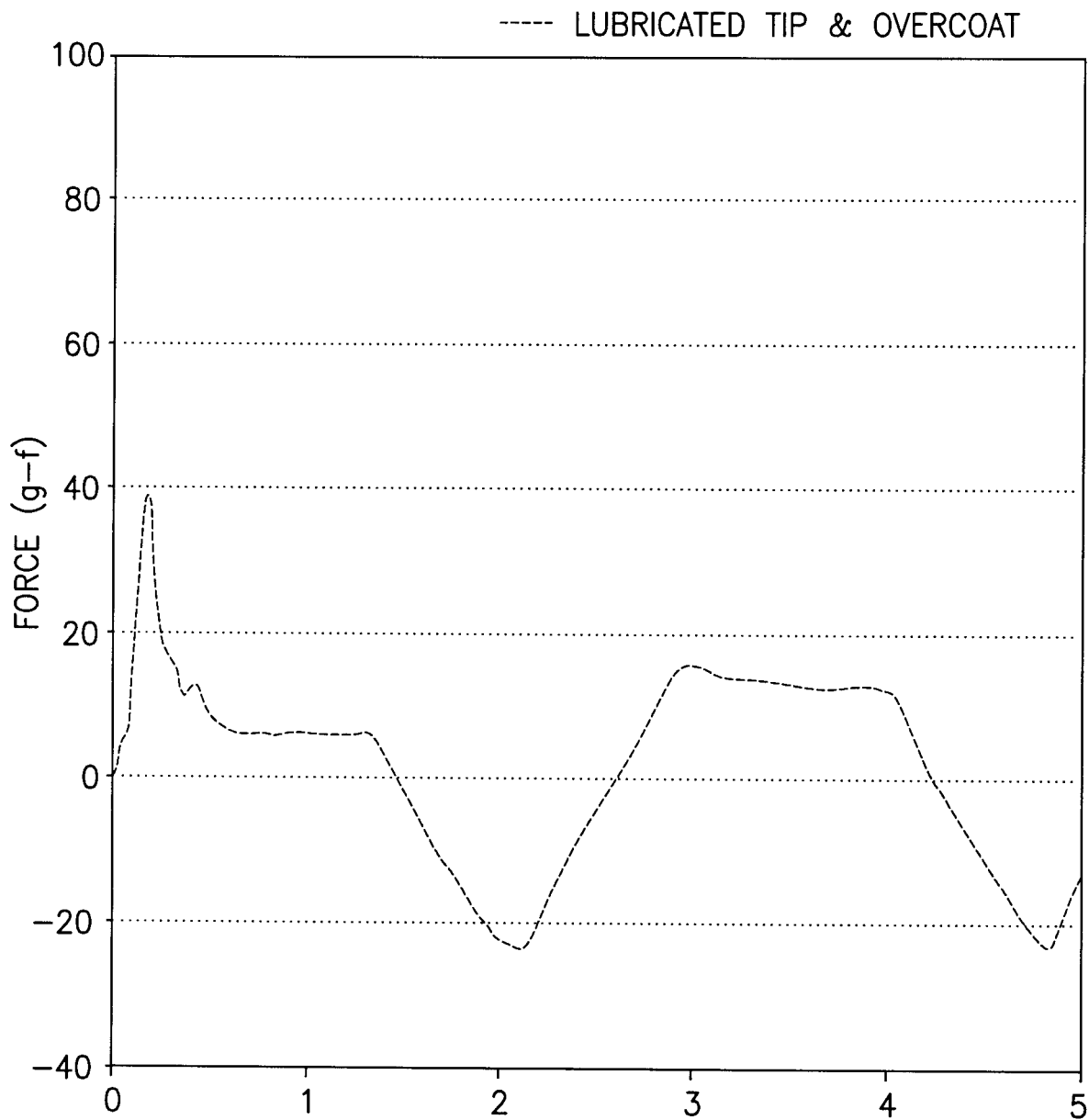

In this example, a needle as in Example 1 was used where the tip of the needle was coated with a crosslinked lubricant and the body of the needle was coated with a non-crosslinked lubricant as an overcoat layer. As shown in FIG. 12A and FIG. 12B, the lubricated tip provides a significantly reduced peak penetration force corresponding to an initial insertion force and maintains a relatively low drag force. In this example, the drag force is sufficient to inhibit free movement of the needle in the substrate after insertion.

Figure 13:
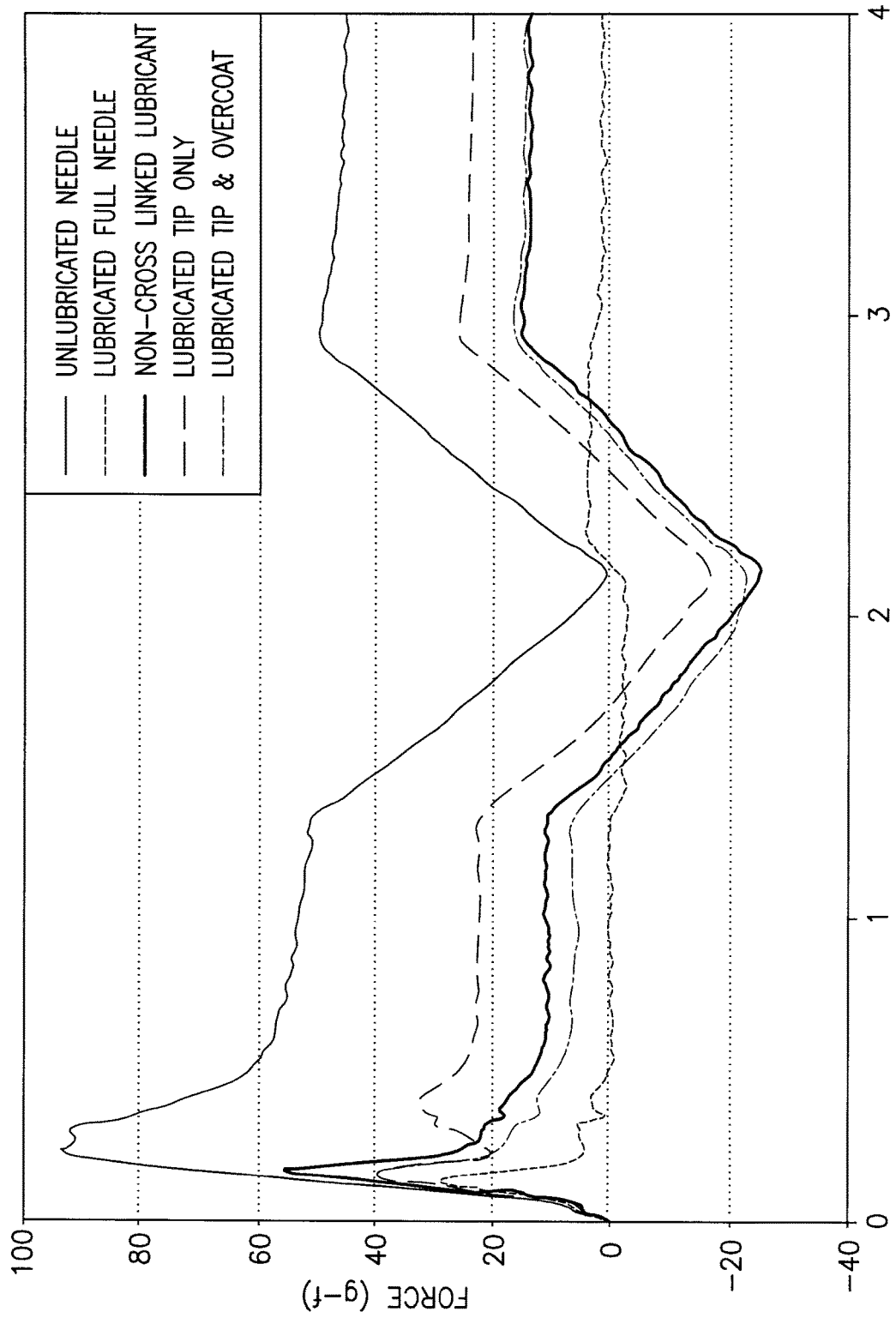
FIG. 13 is a graph comparing the data of Examples 1-5.

Each of the measurements obtained according to Examples 1-5 are overlaid in a single plot in FIG. 13. As shown in the data, the needle in Example 5 having a crosslinked lubricant on the tip of the needle and a non-crosslinked lubricant overlying the body of the needle provided a low initial penetration force and a drag resistance during the pushing and pulling of the needle such that the drag resistance indicates a coefficient of friction of the needle sufficient to resist movement between the needle and the tissue at an insertion site after insertion.

As demonstrated in the examples, it has been found that a single coating of an uncrosslinked lubricant provides sufficient lubricity to reduce the peak penetration force (PPF) during the initial insertion into the tissue. However, the uncrosslinked lubricant is removed from the surface of the medical device quickly to expose the surface of the medical device which then exhibits high drag forces on the tissue. The high drag forces on the tissue result in inflammation and irritation of the tissue. A highly lubricious coating on the medical device formed from a crosslinked lubricant retains the highly lubricious surface after insertion. Such a highly lubricious surface allows excessive and continuous movement at the tissue interface which also can cause irritation and inflammation. It has been found that an outer coating of a lubricant can provide a sufficient lubricity for insertion and penetration of the medical device in the tissue and an inner coating or surface texture having a lower lubricity or coefficient of friction greater than the coefficient of friction of the outer lubricant to provide the needed resistance to movement during normal use and movement by the patient to inhibit irritation and inflammation of the tissue, while providing sufficient lubricating properties to allow removal of the medical device without excessive pain and discomfort to the patient.

While various embodiments have been chosen to describe the invention, it will be understood by one skilled in the art that various changes and modifications can be made without departing from the scope of the invention as defined in the appended claims.

What is claimed is:

1. A medical device comprising:
   an elongated body having an outer surface, a distal end, a proximal end, and a skin contact area spaced from said distal end, said distal end of said elongated body adapted for inserting into or through a skin of a patient;
   an inner coating of a lubricant on said outer surface at said distal end of said elongated body;
   a removable outer lubricious coating applied on said inner coating and on said skin contact area of said outer surface of said elongated body to assist insertion of said elongated body into said skin, said inner coating formed at said distal end between said outer lubricious coating and said elongated body, said outer coating being removable from said skin contact area of said elongated body and removable from said inner coating by body fluids from said patient to expose said skin contact area of said elongated body and expose said inner coating, said inner coating having a coefficient of friction greater than a coefficient of friction of said outer lubricious coating to resist movement of said elongated body with respect to said skin of said patient after the insertion into the skin and removal of said outer lubricious coating, said inner coating comprising a crosslinked silicone lubricant and said outer lubricious coating comprising a water based uncrosslinked silicone lubricant;
   said outer surface of said elongated body having a coefficient of friction higher than said inner coating and higher than said outer lubricious coating, where said skin contact area of said elongated body inhibits the movement of said elongated body with respect to the skin after the insertion and after the removal of said outer coating from said skin contact area and said inner coating, and to inhibit irritation of the skin at an insertion site.

2. The medical device of claim 1, wherein said elongated body is selected from the group consisting of a cannula, sensor and probe.

3. The medical device of claim 1, wherein said elongated body is a glucose monitoring probe adapted for positioning in or below the skin of the patient to monitor glucose blood levels.

4. The medical device of claim 1, wherein said medical device comprises an intravenous needle.

5. The medical device of claim 1, wherein said skin contact area has a textured surface to inhibit the movement of said elongated body with respect to said skin and inhibit the irritation of said skin after the insertion.

6. The medical device of claim 1, wherein said outer surface of said elongated body includes at least one component for promoting tissue growth at the insertion site.

7. A biosensor probe for penetrating and inserting through a skin of a patient, said biosensor probe comprising:
   an elongated body having a sensor for detecting an analyte, a proximal end, a distal end and an outer surface with a skin contact area spaced from said distal end;
   an inner coating of a lubricant applied on said outer surface at a tip of said distal end of said elongated body, and a removable outer coating of a lubricant overlying said inner coating and said skin contact area of said elongated body to assist penetration and insertion through the skin of said patient, said outer coating being removable during or after the insertion into the patient to expose said skin contact area and to expose said inner coating; and said skin contact area of said elongated body being spaced from said inner coating at said tip, said skin contact area having a surface adapted for contacting the skin and having a coefficient of friction higher than a coefficient of friction of said inner coating and higher than a coefficient of friction of said outer coating to resist movement of said elongated body relative to the skin after the insertion and after removal of said outer coating, said inner coating comprising a crosslinked silicone lubricant having a coefficient of friction greater than said coefficient of friction of said outer coating-, and said outer coating comprising a water-based uncrosslinked silicone lubricant whereby said outer coating is removable from said inner coating and said skin contact area of said elongated body during or after the insertion of said elongated body into said skin to expose said inner coating and to expose said skin contact area to inhibit the movement of said elongated body relative to said skin at an insertion site in the patient after the removal of said outer coating.

8. The biosensor probe of claim 7, wherein
said outer coating is removable from said elongated body by contact with body fluids of the patient to expose the inner coating on the outer surface of the elongated body.

9. The biosensor probe of claim 7, wherein said outer coating is removable by a shearing action by the insertion of said elongated body into the skin.

10. The biosensor probe of claim 7, wherein said outer coating is removable from said elongated body during or after the insertion of said elongated body to expose said outer surface of said elongated body, and where said elongated body has a textured surface to define said outer surface with a coefficient of friction sufficient to inhibit movement between said elongated body and tissue.

11. The biosensor probe of claim 7, wherein
said outer surface of said elongated body includes at least one tissue growth promoting component for promoting tissue growth at the insertion site.

* * * * *